United States Patent [19]

Mather et al.

[11] 4,191,704

[45] * Mar. 4, 1980

[54] HIGHLY CONCENTRATED ALKYL SULPHATE SOLUTIONS POURABLE AT AMBIENT

[75] Inventors: Douglas E. Mather, Whitehaven; Edward T. Messenger, High Harrington; Bryn M. Phillips, Whitehaven, all of England

[73] Assignee: Albright & Wilson Ltd., Warley, United Kingdom

[*] Notice: The portion of the term of this patent subsequent to Nov. 25, 1996, has been disclaimed.

[21] Appl. No.: 809,709

[22] Filed: Jun. 24, 1977

Related U.S. Application Data

[63] Continuation of Ser. No. 708,963, Jul. 26, 1976, abandoned, which is a continuation-in-part of Ser. No. 541,371, Jan. 15, 1975, abandoned.

[30] Foreign Application Priority Data

Jan. 16, 1974 [GB] United Kingdom ............... 02038/74

[51] Int. Cl.$^2$ ........................................... C07C 141/04
[52] U.S. Cl. ................................................. 260/459 R
[58] Field of Search ................................... 260/459 R

[56] References Cited

U.S. PATENT DOCUMENTS

| 2,052,027 | 8/1936 | Harris | 260/459 R |
| 2,256,877 | 9/1941 | Bertsch | 260/459 R |
| 3,413,331 | 11/1968 | Beiser et al. | 260/459 R |

*Primary Examiner*—Joseph E. Evans
*Attorney, Agent, or Firm*—Frishauf, Holtz, Goodman & Woodward

[57] ABSTRACT

Alkyl sulphates are prepared in a high concentration by mixing together an alkyl sulphuric acid and ammonium or an amine in the presence of sufficient water to maintain the product in the G phase above the minimum concentration at which gel formation is encountered.

13 Claims, No Drawings

HIGHLY CONCENTRATED ALKYL SULPHATE SOLUTIONS POURABLE AT AMBIENT

This is a continuation of application Ser. No. 708,963, filed July 26, 1976 and now abandoned, which is a Continuation-in-Part of application Ser. No. 541,371 filed Jan. 15, 1975 and now abandoned.

The present invention relates to the manufacture of alkyl sulphates in highly concentrated aqueous solutions.

Hitherto alkyl sulphates for use as surfactants have been prepared by reacting a fatty alcohol with a sulphating reagent such as $ClSO_3H$ to form an acid ($RSO_4H$ where R is an alkyl group) and neutralising the acid with a dilute aqueous base. It has been found essential, higherto, to use dilute bases, because the viscosity of aqueous solutions of alkyl sulphates has been observed to increase sharply with increasing concentrations, until a concentration is reached when the product becomes too viscous to handle and forms a gel which makes it impossible to obtain adequate mixing of the aqueous base with the acid. This concentration depends on the material, and is usually in the region 25–45%.

For this reason alkyl sulphates have hitherto been prepared only in dilute solutions, despite the obvious disadvantages of such solutions for the purposes of storage and transport. It has generally been considered impossible to make alkyl sulphates above a critical concentration which varies according to the material but in a typical case (e.g. $R=C_{12}$ to $_{14}$) is about 30 to 45% by weight. Attempts to prepare more concentrated solutions with the aid of viscosity modifying additives have had only very limited success. It has not been possible, hitherto, to prepare significantly more concentrated solutions at elevated temperatures, since it has been found that if the concentration is substantially higher than the critical limit heating does not make the solution fluid but merely tends to cause hydrolysis.

It has been reported that sodium lauryl sulphate forms a liquid crystal phase known as the lamellar or G phase at specific high concentrations and elevated temperatures of about 74° C. This G phase is pourable, but in view of the elevated temperature required the phenomenon has been of purely academic interest and has not been applied in industry.

Surprisingly we have now discovered that if the concentration of certain economically important alkyl sulphates is increased to the region of 60–80% at ambient temperature, the viscosity decreases sharply until a point is reached at which the solution is sufficiently fluid to pour readily. We believe that this is due to the formation of a G phase at ambient temperature.

With further increase in concentration the viscosity passes through a minimum and increases sharply, so that the solution again sets into a gel, or similar non-pourable state. Surprisingly we have found that we can obtain such alkyl sulphates as fluid products at a concentration not hitherto manufactured without the assistance of viscosity modifiers. These desirable products may be produced by mixing the acid sulphate with an aqueous base of the required concentration, in such a manner as to maintain the concentration of the product within the fluid region.

The concentration at which the minimum occurs varies according to the particular alkyl sulphate and its purity. The presence of impurities, e.g. unsulphated alcohol or excess sulphate ion, tends to alter the position of the minimum.

Our invention provides a method for the preparation of alkyl sulphates which comprises mixing together an acid of the formula $RSO_4H$ where R is an alkyl group having an average of up to 18 carbon atoms and a base selected from ammonia and amines having from 1 to 6 carbon atoms in the presence of sufficient water to maintain the product in the G phase.

The alkyl sulphuric acid is often a mixture of acids of different carbon chain lengths e.g. wherein R has an average of from 8 to 18 carbon atoms, e.g. 12 to 16 carbon atoms. Typical examples of suitable acids are those obtained by the sulphation of dodecyl, hexadecyl, or octadecyl alcohols or mixtures thereof such as may be obtained from palm kernal oil or coconut oil. Preferably the alkyl group is straight chain, but branched chain alkyls can also be used.

The base may be ammonium hydroxide, or an organic amine e.g. methylamine, ethylamine, dimethylamine, diethylamine, trimethylamine, propylamine, isopropylamine, N-methyl propylamine, or especially an alkylolamine e.g. monoethanolamine, diethanolamine or triethanolamine.

Mixtures of bases may be employed.

The base is typically employed as an aqueous solution whose concentration depends on the amount of water required to form the concentrated liquid state. The appropriate concentration in any particular instance may be determined for example by running a series of test preparations and a graph of viscosity against concentration may then be plotted in order to locate the position of the minimum. The minimum occurs generally at a concentration between 60 and 90% weight of active ingredient, usually between 65 and 85%. Typically a pourable concentrated liquid state is obtained at concentrations within about ±5% of the value corresponding to the viscosity minimum. This range varies to some extent according to the material.

The neutralisation is preferably carried out in a reactor in which a substantial proportion of the product is recycled, as has been employed hitherto for preparing conventional relatively dilute alkyl sulphates, except for the reduced amount of water present, in order to obtain the G phase. The relative proportions of acid and base are usually adjusted to provide a product of a desired pH. Typically the pH aimed for is above 6.5, to avoid decomposition of the product by acid hydrolysis, and up to 8.5. Higher pH's are possible but not usually desirable, commercially, since they result in products that are too caustic for many of the most common end uses of alkyl sulphates.

It is preferred though not essential to carry out the reaction in a "neutralisation loop" system, involving a continuous flow reactor with recycle of a substantial proportion of the product to the reactor. Preferably the acid, an aqueous solution of the base and the recycled product are separately fed to a reactor provided with means for mixing, such as a stirrer. The temperature in the reactor may conveniently be controlled by providing heat exchangers to cool the reaction mixture and/or the recycled product.

The invention makes it possible to prepare the alkyl sulphates as a concentrated aqueous solution, about twice as concentrated as the corresponding prior art commercial alkyl sulphates. The products may be handled in substantially the same way, as free flowing liquids. The invention includes the preparation of mixtures of the ammonium or amine alkyl sulphates with up to about 50% preferably up to about 25% by weight of sodium and/or potassium alkyl sulphates, where such mixtures form a G phase at ambient temperatures. Such mixtures may be prepared by neutralising the alkyl sulphate with two or more bases, preferably in admixture.

The invention is illustrated by the following examples, in which loop neutraliser was employed substantially as hereinbefore described. All percentages are by weight unless otherwise stated.

EXAMPLE 1

A sulphated mixture of C12 and C14 alcohols, neutralised with monoethanolamine was found to exhibit a pourable state at ambient temperature and concentrations of about 82%.

A sulphated mixture of dodecyl and tetradecyl alcohols was used as the acid feed and a solution of 61 g. monoethanolamine per 43.3 g water as the base feed. The feed rates were adjusted to provide a pH of 7.5 and a combined flow rate of 11.5 g per minute. The temperature was maintained at 32° C.

The pourable and pumpable liquid product contained 82.8% of active ingredient having a molar weight of 335, 1.95% fatty matter and 0.83% sulphate as $SO_4$=ion.

EXAMPLE 2

To illustrate the effect of a lower purity acid feed, Example 1 was repeated using a similar acid sulphated to a lower conversion. The viscosity minimum was found to occur at about 74% concentration.

The base feed contained 61 gs. monoethanolamine per 59 gs. water. The feed rates were adjusted to provide a pH of 7.5 and a combined flow of 12 gs. per minute. The product contained 75.7% of active ingredient having molar weight of 335, 3.2% free fatty material and 2% sulphate as $SO_4$=ion. The product was pourable liquid at the ambient temperature, but solidified at 13° C.

EXAMPLE 3

Example 1 was repeated using ammonia instead of monoethanolamine. The ammonium salt formed a concentrated liquid phase at ambient temperatures.

The base feed contained 48.6 gs. of concentrated aqueous ammonia (e.g. 0.880) in 66.7 gs. water. The pH of the product was 7.5 and the combined feed rate was 52 gs./min. The temperature was maintained at 35° C. The pourable liquid product contained 62% of active ingredient having a molar weight of 295, 3.2% of free fatty material and 1.1% of sulphate as $SO_4$=ion. The product was liquid above 18° C.

EXAMPLE 4

Example 1 was repeated using a mixed base feed containing 12.5 grammes monoethanolamine, 20.8 grammes of commercial triethanolamine and 32.4 grammes concentrated ammonia (S.G. 0.880) in 34 grammes water. The temperature was maintained at 30° C. and the combined flow rate was 10 gs./min.

The product contained 73.1% of active ingredient having molar weight of 321, 3.7% of free fatty material and 1.8% of sulphate as $SO_4$=ion. It was a pourable liquid at temperatures above 15° C.

EXAMPLE 5

A sulphated mixture of C12 and C14 alcohols, neutralised with dimethylamine was found to exhibit a pourable state at ambient temperature and concentrations of about 74%.

A sulphated mixture of dodecyl and tetradecyl alcohols was used as the acid feed and a solution of 45 g dimethylamine per 80.3 g water as the base feed. The feed rates were adjusted to provide a pH of 7.5 and a combined flow rate of 12.5 g per minute. The temperature was maintained at 35° C.

The pourable and pumpable liquid product contained 74.2% of active ingredient having a molar weight of 332, 1.55% fatty matter and 1.3% sulphate as $SO_4$=ion.

EXAMPLE 6

The process of Example 5 was repeated using triethylamine as the base, the G phase formed at a concentration of 89% active material. The alkyl sulphuric acid was neutralised with 102 gm of triethylamine in 20.0 gm water. The product contained 89.3% by weight active material having molecular weight of 377 and 3.25% fatty material with 1.06% by weight sulphate ion. The product was fluid at 11° C.

For comparison attempts to neutralise a C12 to C14 alkyl sulphuric acid with sodium hydroxide at concentrations above 60% and at 30° C. failed due to the viscosity of the material. A liquid state above 60% concentration could not be obtained below about 80° C.

However, a mixture of 10 parts by weight sodium hydroxide and 90 parts monoethanolamine give a mixed salt which formed a pourable G phase at 11° C.

We claim:

1. A method for the preparation of aqueous solutions of gel-forming alkyl sulphates which contain concentrations of alkyl sulphate greater than 60% by weight and which are pourable at ambient temperatures which consists essentially in mixing an acid of the formula $RSO_4H$, where R is an alkyl group, having an average of 12 to 16 carbon atoms and a sufficient amount of a base selected from the group consisting of ammonium hydroxide and alkylamines and alkylolamines having a total of up to six carbon atoms and mixtures thereof to provide a final pH of between 6.5 and 8.5 and in the presence of sufficient water to maintain the product in the G phase.

2. A method according to claim 1 which comprises passing a continuous stream of the base and the water and a continuous stream of the acid to a mixing zone, mixing the aqueous base and the acid in the mixing zone, passing the mixture as a continuous stream to a separating zone, separating the mixture into a product stream and a recycle stream and passing the recycle stream to the mixing zone.

3. A method according to claim 1 wherein R s an n-alkyl group.

4. A method according to claim 1 wherein the base is ammonium hydroxide.

5. A method according to claim 1 wherein the base is dimethylamine.

6. A method according to claim 1 wherein the base is monoethanolamine.

7. A method according to claim 1 wherein the base is triethanolamine.

8. A method according to claim 1 wherein the base is a mixture of ammonium hydroxide, monoethanolamine and triethanolamine.

9. A method according to claim 1 for the preparation of ammonium alkyl sulphates which consists essentially in mixing an n-alkyl sulphuric acid having an average of from 12 to 16 carbon atoms per molecule with sufficient ammonium hydroxide to provide a final pH of between 6.5 and 8.5 in the presence of sufficient water to provide a final concentration of about 83% by weight of the alkyl sulphate such that the product is in the G phase.

10. An aqueous solution of more than 60% by weight of an n-alkyl sulphate wherein the alkyl group has an average of from 12 to 16 carbon atoms of a base selected from the group consisting of ammonium hydroxide, methylamine, dimethylamine, trimethylamine, ethylamine, diethylamine, triethylamine, monoethanolamine, diethanolamine, triethanolamine and mixtures thereof, said solution being in the form of a pourable G phase at ambient temperatures.

11. An aqueous solution according to claim 10 wherein said base is ammonium hydroxide.

12. An aqueous solution according to claim 10 wherein said base is monoethanolamine.

13. An aqueous solution according to claim 10 wherein said base is dimethylamine.

* * * * *

UNITED STATES PATENT AND TRADEMARK OFFICE
CERTIFICATE OF CORRECTION

PATENT NO. : 4,191,704
DATED : March 4, 1980
INVENTOR(S) : Douglas E. Mather et al It is certified that error appears in the above—identified patent and that said Letters Patent is hereby corrected as shown below:

Column 3, line 21, "43.3 g" should read -- 48.3 g --.

Column 3, line 38, "75.7%" should read -- 73.7% --.

Signed and Sealed this

Thirtieth Day of September 1980

[SEAL]

Attest:

SIDNEY A. DIAMOND

Attesting Officer

Commissioner of Patents and Trademarks